United States Patent [19]

Baker et al.

[11] 4,081,474
[45] Mar. 28, 1978

[54] SULFONYLOXY BROMOACETANILIDES AND THEIR UTILITY AS BIOCIDES

[75] Inventors: Don R. Baker, Orinda; Eugene G. Teach, El Cerrito, both of Calif.

[73] Assignee: Stauffer Chemical Company, Westport, Conn.

[21] Appl. No.: 718,997

[22] Filed: Aug. 30, 1976

Related U.S. Application Data

[60] Continuation of Ser. No. 612,404, Sep. 11, 1975, abandoned, which is a continuation of Ser. No. 470,504, May 16, 1974, abandoned, which is a division of Ser. No. 288,235, Sep. 11, 1972, Pat. No. 3,836,564, which is a continuation-in-part of Ser. No. 127,775, Mar. 24, 1971, abandoned, which is a division of Ser. No. 806,717, Mar. 12, 1969, abandoned.

[51] Int. Cl.$^2$ .......................................... C07C 143/68
[52] U.S. Cl. ................................................. 260/456 A
[58] Field of Search ................................... 260/456 A

[56] References Cited

U.S. PATENT DOCUMENTS

| | | | |
|---|---|---|---|
| 3,032,555 | 5/1962 | Oxley et al. | 260/268 |
| 3,687,998 | 8/1972 | Trepka | 260/456 A |
| 3,818,102 | 6/1974 | Partos | 260/456 P |
| 3,836,564 | 9/1974 | Baker et al. | 260/456 |
| 3,850,972 | 11/1974 | Goralski | 260/456 P |

OTHER PUBLICATIONS

Sen et al., J. Indian Chem. Soc., 42, 563 (1965).
Ozawa et al., Chem. Abstract, 47, 10805i–10806d (1953).
Surrey et al., J. Am. Chem. Soc., 77, 3798 (1956).

*Primary Examiner*—Nicky Chan
*Attorney, Agent, or Firm*—Harry A. Pacini

[57] ABSTRACT

Sulfonyloxy bromoacetanilides as new compositions and their activity as microbiocides. Representative compounds include m-isobutyl-sulfonyloxy bromoacetanilide and m-phenyl-sulfonyloxy bromoacetanilide.

2 Claims, No Drawings

SULFONYLOXY BROMOACETANILIDES AND THEIR UTILITY AS BIOCIDES

This is a continuation, of application Ser. No. 612,404, filed Sept. 11, 1975 now abandoned; which in turn is a continuation of Ser. No. 470,504, filed May 16, 1974, now abandoned; which in turn is a continuation of Ser. No. 470,504, filed May 16, 1974, now abandoned; which in turn is a division of Ser. No. 288,235, filed Sept. 11, 1972, now U.S. Pat. No. 3,836,564; which in turn is a continuation-in-part of copending application Ser. No. 127,775, filed Mar. 24, 1971, now abandoned; which in turn is a division of then copending application Ser. No. 806,717, filed Mar. 12, 1969, now abandoned.

This invention relates to certain new organic compounds which are useful as effective biostatic agents. More specifically, this invention relates to certain bromoacetanilides and their utility in bacteriostatic and fungistatic compositions.

The compounds of the instant invention correspond to the general formula

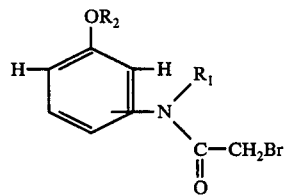

wherein $R_1$ is hydrogen or lower alkyl having from 1 to about 4 carbon atoms, inclusive, $R_2$ represents (1) hydrogen;

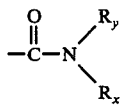 (2)

in which $R_x$ and $R_y$ are independently hydrogen, alkyl, allyl, lower alkoxyalkyl, cyclohexyl, 2-chloroallyl, phenyl, benzyl, or substituted-phenyl in which the substituents are chloro, nitro, lower alkyl, lower alkoxy or cyano, $R_x$ and $R_y$ taken together represents an alkylene containing 4 to 6 carbon atoms, inclusive, or lower alkyl-substituted alkylene containing a total of 5 to 8 carbon atoms, inclusive;

 (3)

in which $R_A$ is alkyl, phenyl, substituted-phenyl in which the substituents are chloro, nitro, lower alkyl, lower alkoxy or cyano;

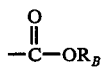 (4)

in which $R_B$ is alkyl, phenyl, substituted-phenyl in which the substituents are chloro, nitro, lower alkyl, lower alkoxy or cyano;

 (5)

in which $R_C$ is hydrogen, alkyl, haloalkyl, phenyl, substituted phenyl in which the substituents are chloro, nitro, lower alkyl, lower alkoxy or cyano; provided that when $R_2$ is hydrogen and $R_1$ is hydrogen, then the group

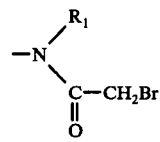

is substituted in the meta-position; and provided that when $R_2$ is

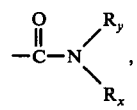, then the group

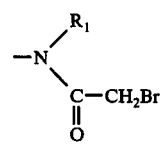

is in the meta-position. The above compounds as well as compounds in which $R_2$ is hydrogen and $R_1$ is hydrogen and

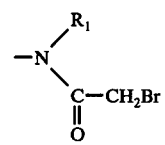

is in the para-position, are effective microbiocides.

In the above description, the following preferred embodiments are intended for the various groups. Alkyl preferably includes, unless otherwise provided for, those members which contain from 1 to about 6 carbon atoms, inclusive, in both straight chain and branched chain configurations, for example, methyl, ethyl, n-propyl, isopropyl, n-butyl, sec.-butyl, amyl, isoamyl, n-hexyl, isohexyl, and the like; and lower alkoxyalkyl preferably includes those members which contain a total of not more than 6 carbon atoms, for example, methoxymethyl, methoxyethyl, ethoxymethyl, methoxypropyl, ethoxypropyl, propoxypropyl, ethoxybutyl, methoxyamyl, and the like. Haloalkyl preferably includes those alkyl members which contain from 1 to about 4 carbon atoms, inclusive, and are substituted with at least one halogen such as chlorine, bromine and iodine. Lower alkyl and lower alkoxy preferably include those members which contain from 1 to about 4 carbon atoms, inclusive, in either straight chain or branched chain configurations.

The compounds herein described can be prepared by one of several methods, depending upon the nature of the starting materials and products desired. The compound 3'-hydroxybromoacetanilide within the scope of this invention can be conveniently prepared by the condensation of m-aminophenol and bromoacetyl bromide. This preparation is specifically described in Example I below. Starting with either the 3'- or 4'- hydroxybromacetanilide, subsequent condensation reactions can be performed which will ultimately yield other members of this series. Generally, these reactions are performed in a suitable solvent, such as benzene, toluene, acetone, methylethyl ketone and the like. The monosubstituted carbamate condensation reactions are carried out employing the appropriate isocyanate in the presence of catalysts, such as triethylene diamine and dibutyltin dilaurate, in order to facilitate the completion of the reaction. Alternatively, the carbamate derivatives disclosed herein, preferably when $R_x$ and $R_y$ are both hydrogen, are prepared by conversion of the substituted-phenol to the corresponding chloroformate using phosgene, followed by reaction with the appropriate primary or secondary amine or ammonia. The preparation of the sulfonate, dialkyl carbamate, carbonate and carboxylate derivatives are prepared using the appropriate acid halide and an acid acceptor such as pyridene, triethylamine, sodium bicarbonate and the like. After the reaction is completed, the solvent is removed and the product recovered therefrom. Upon isolation of the crude product, final recovery of the purified material is accomplished by normal workup procedures, such as crystallization or distillation.

It has been found that the compounds as defined supra are effective bacteriostatic and fungistatic agents. Whereas microbiological growths on various substances cause deterioration by the presence of the infestation, the application of an agent to retard this adverse growth is desired. Such substances liable to fungus and bacterial infection include cloth, leather, paint, soaps, paper, wood, plastic, oil, and the like. It is contemplated herein that the microbiocidal compositions of the present invention may be effectively incorporated or applied to any of the substances susceptible to microbiological growths.

For maximum effectiveness, the active ingredients of the present invention are admixed in microbiostatically effective amounts with an inert adjuvant. In order to provide formulations particularly adapted for ready and efficient application to the materials to be treated, such formulations comprise those of both the liquid and solid types as well as the "aerosol" type formulations. Application can be directly to the substance to be protected from fungus and bacterial growth. In the pure state, the active ingredient may be too effective or too potent in some applications to have practical utility. A convenient method of treating cloth is by formulating the active ingredient with a soap or detergent and thereby imparting antiseptic or microbiocidal properties to the clotch as it is washed therewith.

For most effective protection it is preferred to apply the materials in intimate contact but thoroughly dispersed on or nearly in the surface to be protected. Therefore, the active ingredients have incorporated therewith a relatively inert agent or adjuvant as a dispersing medium, utilizing methods well known to those skilled in the art.

Suitable formulations of the compounds of this invention comprise the above-defined active ingredients and a suitable material as an adjuvant therefor. Fungistat and bacteriostat compositions are advantageously formulated by first preparing a solution thereof in an organic solvent and then adding the resulting solution to water or other carrier. If necessary, an emulsifying agent may be employed. The compositions may also be incorporated into solid carriers such as clay, talc, pumice, soap, and the like. They may also be dissolved in liquefied gases such as fluorochloroethanes or methyl chloride and applied from aerosol bombs containing the solution. It should be noted that suitable formulations may also include adhesive agents, inddicators, and other microbiocidal ingredients. Other ingredients may be supplementary insecticides, fungicides, bacteriocides, nematocides or selective herbicides.

Since the amount of active agent of the present invention which is employed will vary with the microbiocidal effect sought, the utility of the treated material, type and dimensions of the material treated, it is evident that no rigid limits can be set forth on the quantity required. Determination of the optimum effective concentration for a specific performance is readily ascertainable by routine procedures, as will be apparent to those skilled in the art.

Preparation of the compounds of the present invention are illustrated by the following particular examples. Following the examples is a table of compounds which are prepared according to the procedures described herein.

EXAMPLE I

Preparation of 3'-hydroxybromoacetanilide m-Aminophenol, 66.5 g. (0.61 mole), is dissolved in 500 ml. of a 50/50 (v/v) mixture of glacial acetic acid and saturated sodium acetate solution. The mixture is cooled to approximately 10° C. and 200 g. (0.99 mole) of bromoacetyl bromide is added dropwise. The temperature is maintained between 15° and 20° C. When addition is complete, the mixture is stirred while cooling until the temperature is about 5° C. The product is filtered off, washed successively with cold water, saturated sodium bicarbonate solution and finally two portions of water. The product is dried under vacuum. The yield of the title compound is 121 g. (86 percent of theory), m.p. 167°–170° C.

EXAMPLE II

Preparation of 3'-N-methyl carbamoyloxy bromoacetanilide 3-hydroxybromoacetanilide, 34.5 g. (0.15 mole) in 250 ml. of acetone containing approximately 100 mg. of triethylene diamine and 5 drops of dibutylin dilaurate is refluxed for 2 hours with 9.4 g. (0.165 mole) of methyl isocyanate. On cooling, the product crystallizes from solution and is recovered by filtration. There is obtained 24 g. (56 percent of theory) of the title compound. m.p. 136°–138° C.

EXAMPLE III

Preparation of m-Isobutylsulfonyloxy bromoacetanilide

To 3'-aminophenyl isobutyl sulfonate, 6.9 g. in 100 ml. of methylene chloride is added 6.1 g. of bromoacetyl bromide. The resulting solution is cooled and 3.1 g. of triethylamine is added dropwise. The product is recovered by washing with cold water, drying and removal of the solvent. There is obtained 8.9 g. of the title compound, $n_D^{30} = 1.5500$.

EXAMPLE IV

Preparation of m-Phenylsulfonyloxy bromoacetanilide

To a mixture of 4.4 g. of benzene sulfonyl chloride and 5.7 g. of 3'-hydroxy bromoacetanilide in 100 ml. of methylene chloride is added dropwise 2.6 g. of triethylamine. The product is recovered by washing with cold water, drying and removal of the solvent. There is obtained 9.0 g. of the title compound, $n_D^{30} = 1.5830$.

TABLE I

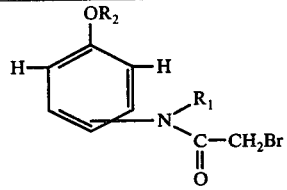

| COMPOUND NUMBER | $R_1$ | $R_2$ | Position | m.p. °C. or $n_D^+$ |
|---|---|---|---|---|
| 1 | H | H | meta | 167–170 |
| 2 | H | C(O)NHCH$_3$ | meta | 136–138 |
| 3 | H | C(O)NHCH(CH$_3$)$_2$ | meta | 144–149 |
| 4 | H | C(O)NHCH$_2$CH=CH$_2$ | meta | 122–125 |
| 5 | H | C(O)NH(cyclohexyl) | meta | 163–165 |
| 6 | H | H | para | 141–144 |
| 7 | H | S(O$_2$)i-C$_4$H$_9$ | meta | 1.5500 |
| 8 | H | S(O$_2$)phenyl | meta | 1.5830 |

Other examples of compounds falling within the generic formula presented herein, which are preparable by the aforedescribed and which may be formulated into microbiocidal compositions and applied as herein illustrated, are:

| COMPOUND NUMBER | $R_1$ | $R_2$ | Position |
|---|---|---|---|
| 9 | C$_2$H$_5$ | H | meta |
| 10 | H | C(O)NH$_2$ | meta |
| 11 | CH$_3$ | C(O)NHCH$_3$ | meta |
| 12 | H | C(O)N(CH$_3$)$_2$ | meta |
| 13 | H | C(O)NH-n-C$_4$H$_9$ | meta |
| 14 | H | C(O)N(n-C$_4$H$_9$)$_2$ | meta |
| 15 | C$_2$H$_5$ | C(O)NH$_2$ | meta |
| 16 | C$_2$H$_5$ | C(O)NHCH$_3$ | meta |
| 17 | C$_2$H$_5$ | C(O)N(CH$_3$)$_2$ | meta |
| 18 | C$_2$H$_5$ | C(O)N(n-C$_4$H$_9$)$_4$ | meta |
| 19 | CH$_3$ | C(O)N(CH$_2$CH=CH$_2$)$_2$ | meta |
| 20 | CH$_3$ | C(O)N=(CH$_2$)$_6$ | meta |
| 21 | H | C(O)NH(phenyl) | meta |
| 22 | C$_2$H$_5$ | C(O)NH(phenyl) | meta |
| 23 | H | C(O)NH(CH$_2$CH$_2$OCH$_3$) | meta |
| 24 | C$_2$H$_5$ | C(O)NH(CH$_2$CH$_2$OC$_2$H$_5$) | meta |
| 25 | H | C(O)NH(benzyl) | meta |
| 26 | C$_2$H$_5$ | C(O)NH(benzyl) | meta |
| 27 | H | C(O)NH(CH$_2$CCl=CH$_2$) | meta |
| 28 | C$_2$H$_5$ | C(O)NH(CH$_2$CCl=CH$_2$) | meta |
| 29 | H | C(O)NH(p-NO$_2$-phenyl) | meta |
| 30 | C$_2$H$_5$ | C(O)NH(p-NO$_2$-phenyl) | meta |
| 31 | H | C(O)NH(p-Cl-phenyl) | meta |
| 32 | C$_2$H$_5$ | C(O)NH(m-Cl-phenyl) | meta |
| 33 | H | C(O)N(2-methylpiperidinyl) | meta |
| 34 | C$_2$H$_5$ | C(O)N(2-methylpiperidinyl) | meta |
| 35 | H | S(O$_2$)CH$_3$ | para |
| 36 | C$_2$H$_5$ | S(O$_2$)C$_2$H$_5$ | meta |
| 37 | H | C(O)OCH$_3$ | meta |
| 38 | H | C(O)OCH$_3$ | para |
| 39 | C$_2$H$_5$ | C(O)OCH$_3$ | para |
| 40 | C$_2$H$_5$ | C(O)OCH$_3$ | meta |
| 41 | C$_2$H$_5$ | C(O)OC$_2$H$_5$ | para |
| 42 | H | C(O)OC$_2$H$_5$ | meta |
| 43 | H | C(O)H | meta |
| 44 | H | C(O)H | para |
| 45 | C$_2$H$_5$ | C(O)H | meta |
| 46 | C$_2$H$_5$ | C(O)H | para |
| 47 | H | C(O)C$_2$H$_5$ | meta |
| 48 | C$_2$H$_5$ | C(O)C$_2$H$_5$ | meta |
| 49 | C$_2$H$_5$ | C(O)CH$_3$ | para |
| 50 | C$_2$H$_5$ | S(O$_2$)phenyl | meta |
| 51 | H | S(O$_2$)(p-Cl-phenyl) | meta |
| 52 | C$_2$H$_5$ | S(O$_2$)(m-Cl-phenyl) | para |
| 53 | H | S(O$_2$)(m-NO$_2$-phenyl) | meta |
| 54 | H | S(O$_2$)(CH$_3$-phenyl) | meta |
| 55 | H | S(O$_2$)(p-CH$_3$O-phenyl) | meta |
| 56 | i-C$_3$H$_7$ | S(O$_2$)(p-CN-phenyl) | meta |
| 57 | H | S(O$_2$)(p-Br-phenyl) | meta |
| 58 | H | C(O)O-phenyl | meta |
| 59 | i-C$_3$H$_7$ | C(O)O(p-Cl-phenyl) | para |
| 60 | H | C(O)O(m-NO$_2$-phenyl) | meta |
| 61 | CH$_3$ | C(O)O(p-CH$_3$-phenyl) | meta |
| 62 | H | C(O)O(p-CH$_3$O-phenyl) | meta |
| 63 | CH$_3$ | C(O)O(o-CH$_3$-phenyl) | para |
| 64 | C$_2$H$_5$ | C(O)O(p-CN-phenyl) | para |
| 65 | H | C(O)CH$_2$Br | meta |
| 66 | CH$_3$ | C(O)CH$_2$CH$_2$Cl | meta |
| 67 | H | C(O)-p-Cl-phenyl | para |
| 68 | CH$_3$ | C(O)-m-NO$_2$-phenyl | meta |
| 69 | C$_2$H$_5$ | C(O0-p-CH$_3$-phenyl | para |
| 70 | H | C(O)-p-CH$_3$O-phenyl | para |
| 71 | CH$_3$ | C(O)p-CN-phenyl | meta |
| 72 | H | C(O)-phenyl | meta |
| 73 | C$_2$H$_5$ | C(O)-phenyl | meta |
| 74 | C$_2$H$_4$ | C(O)NH(cyclohexyl) | para |
| 75 | H | C(O)NH(p-CNphenyl) | meta |
| 76 | n-C$_4$H$_9$ | C(O)p-CN-phenyl) | meta |
| 77 | H | C(O)NH(—CH$_3$O-phenyl) | meta |
| 78 | H | C(O)NH(p-CH$_3$O-phenyl) | meta |
| 79 | CH$_3$ | C(O)NH(o-CH$_3$-phenyl) | meta |

As previously mentioned, the herein described compounds are microbiostatic agents which are useful and valuable in controlling fungi and bacteria. The compounds of this invention are tested as microbiocides in the following manner.

In Vitro Vial Tests

The compounds are tested to determine the microbiostatic efficacy when in contact with growing fungi or bacteria in an artifical medium. For each candidate compound, four 1-ounce vials are partially filled, two with malt broth and two with nutrient broth. The compound to be tested is placed in the vials at the desired concentration (expressed in parts per million). The vials containing malt broth are inoculated with water suspensions of spores of the desired fungi, *Aspergillus niger* and *Penicillium italicum,* and cells of the bacteria, *Escherichia coli* and *Staphylococcus aureaus,* are inoculated into the vials containing nutrient broth (one specie of organism per vial). The vials are then sealed and held for one week, after which time the growth of the organisms is observed and noted. The tests are repeated using lower concentrations of the candidate compounds to determine the lowest concentration that can be used and still offer some control of the growth of the organism. Table II shows the results of the in Vitro tests.

TABLE II

| | In Vitro Test Lowest Effective Concentration (p.p.m.) | | | |
|---|---|---|---|---|
| COMPOUND NUMBER | Aspergillus niger | Penicillium italicum | Escherichia coli | Staphylococcus aureus |
| 1 | 100 | (25) | (10) | 10 |
| 2 | >50 | >50 | 50 | 50 |
| 3 | (100) | (25) | 25 | 10 |
| 4 | >50 | 50 | >50 | 50 |

TABLE II-continued

| COMPOUND NUMBER | In Vitro Test Lowest Effective Concentration (p.p.m.) | | | |
|---|---|---|---|---|
| | Aspergillus niger | Penicillium italicum | Escherichia coli | Staphylococcus aureus |
| 5 | >50 | (50) | (50) | 50 |
| 6 | 50 | 50 | 25 | 25 |
| 7 | >50 | 50 | >50 | 50 |
| 8 | >50 | 50 | >50 | 50 |
| A | >500 | (500) | (250) | (250) |
| B | >500 | >500 | >500 | >500 |

( ) = Indicates partial control at this concentration.
A = Chloro/analog of Compound Number 1.
B = Chloro/analog of Compound Number 3.

Microbiocide Testing Procedure Using Agar

This test measures the bactericidal and fungicidal properties of a compound when in contact with a growing bacterium or fungi in an artificial medium. The test is conducted by adding 20 ml. portions of a suitable warm sterile agar solution into 20 × 100 mm. petri dishes. Then, the test compound, in 0.5% acetone solution, is added to the petri dishes at levels of 0.5, 1, 10, 50 and 100 μg/ml. and mixed with the warm mobile agar solution. The treated agar mixture is then allowed to come to room temperature and solidify. Cells of the particular organism are then streaked on the surface of the solidified agar and are then incubated for such lengths of time that untreated samples containing no toxicant show luxurious growth typical of the particular organism. This time varies from 24 hours to one week, depending on the particular organism. The fungi are incubated at 30° C. and the bacteria are incubated at 37° C. Nutrient agar is used as the medium in this test for the bacteria. Potato dextrose agar is used as the medium for the fungi. The table below shows the results when sulfonyloxy bromoacetanilides are employed in this test.

TABLE III

| COMPOUND NUMBER | Microbiocidal Activity in Agar Minimum Inhibitory Concentration (μg/ml.) | | | |
|---|---|---|---|---|
| | Escherichia coli | Staphylococcus aureus | Penicillium italicum | Aspergillus niger |
| 7 | >50 | 50 | (10) | >50 |
| 8 | >50 | 10 | 50 | >50 |

Soap Plug Test

Samples of Compounds No. 1 and 3, and 3,4,4-trichlorocarbanilide (TCC) are incorporated at a level of 1% in sodium stearate using acetone with the slurry. The products are air dried and pressed in a metal tube to form a soap plug approximately 10 mm. in diameter and 2 mm. thick. These are placed on nutrient agar plantes that have been streaked separately with *Escherichia coli* and *Staphylococcus aureaus* cells. The plates are incubated at 37° C. for 17 hours. The radius of the zone of biological inhibition around the soap plug is measured. The data from this test are as follows:

TABLE IV

| COMPOUND NUMBER | Soap Plug Test Zone of Biological Inhibition (mm) | |
|---|---|---|
| | Escherichia coli | Staphylococcus aureus |
| 3 | 2 | 6–8 |
| 1 | 2 | 12–15 |
| TCC | 0 | 5 |
| Blank | 0 | 0 |

Detergent Formulation Test

Samples of Compounds No. 1 and 3 of 10–20 mg. are dissolved in 5 ml. of acetone and added to weighed amounts of a commercial laundry detergent identified as "Tide ®," a trademark owned by Proctor and Gamble (a mixture of lauryl sulfate and alkyl benzenesulfonate with tripolyphosphate as a binder), to give a concentration of 0.2% in the detergent. From these detergent samples, 1 g. is added to 500 ml. of 50° C. tap water. To this wash solution is added 25 g. of laundered white cotton duck and the mixture agitated by stirring for 10 minutes. The cloth samples are hand wrung and each sample twice rinsed with stirring for 10 minutes in 500 ml. of 50° C. tap water. Thereafter, the cloth samples are hand wrung and air dried. Samples (1 inch square approximately) of the treated cloth samples are placed on nutrient agar plates that have been separately streaked with *Staphylococcus aureus, Escherichia coli, Brevibacterium ammoniagenes,* and *Trichophyton mentagrophytes.*

The following controls are included in this test: A blank and a control containing a commercial laundry detergent identified as "Dreft ®," a trademark owned by Proctor and Gamble (active ingredients are sodium doderyl-benzene sulfonate, sodium perborate), which contains the biocide 3,3,4-trichlorocarbanilide (TCC). The plates are incubated at 37° C. for various lengths of time to provide growth for the organisms at which time the zone of biological inhibition around the cloth samples is measured. The radius of the zone of biological inhibition around the cloth samples are reported in the following Table V.

TABLE V

| Sample | Detergent Formulation Test Zone of Biological Inhibition (mm) | | | |
|---|---|---|---|---|
| | Escherichia coli | Staphylococcus aureus | Brevibacterium ammoniagenes | Trichophyton mentagrophytes |
| Blank | 0 | 0 | 0 | 0 |
| "Dreft" Control | 0 | trace | 1 | 0 |
| Compound No. 1 | 2 | 3 | 0 | 1 |
| Compound No. 3 | 0 | 1 | 2–3 | 0 |

What is claimed is:

1. A compound having the formula

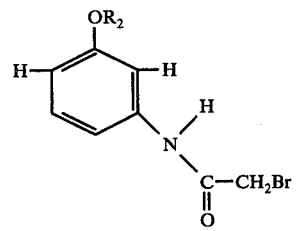

wherein $R_2$ represents

in which $R_A$ is phenyl, and substituted-phenyl in which the substituents are chloro, nitro, and lower alkyl.

2. A compound according to claim 1 in which $R_A$ is phenyl.

* * * * *